(12) United States Patent
Yoshioka

(10) Patent No.: US 7,453,073 B2
(45) Date of Patent: Nov. 18, 2008

(54) METHOD AND EQUIPMENT FOR SPECIMEN PREPARATION

(75) Inventor: Tadanori Yoshioka, Kouchi (JP)

(73) Assignee: Jeol Ltd., Tokyo (JP)

( * ) Notice: Subject to any disclaimer, the term of this patent is extended or adjusted under 35 U.S.C. 154(b) by 434 days.

(21) Appl. No.: 11/237,272

(22) Filed: Sep. 28, 2005

(65) Prior Publication Data
US 2006/0113496 A1    Jun. 1, 2006

(30) Foreign Application Priority Data
Sep. 29, 2004    (JP)    ............... 2004-283802

(51) Int. Cl.
*H01J 37/08*    (2006.01)
(52) U.S. Cl. .............. 250/492.21; 250/492.1; 250/492.22; 250/307; 250/304
(58) Field of Classification Search .... 250/492.1–492.3
See application file for complete search history.

(56) References Cited

U.S. PATENT DOCUMENTS

| | | | |
|---|---|---|---|
| 5,350,499 A | | 9/1994 | Shibaike et al. |
| 5,525,806 A | * | 6/1996 | Iwasaki et al. ......... 250/492.21 |
| 5,629,137 A | * | 5/1997 | Leedy ........................ 430/313 |
| 5,656,811 A | * | 8/1997 | Itoh et al. .................... 250/309 |
| 5,907,157 A | | 5/1999 | Yoshioka et al. |
| 5,916,424 A | * | 6/1999 | Libby et al. ............ 204/298.36 |
| 6,020,677 A | * | 2/2000 | Blanchet-Fincher et al. 313/336 |
| 6,080,991 A | | 6/2000 | Tsai |
| 6,395,347 B1 | | 5/2002 | Adachi et al. |
| 2004/0164242 A1 | | 8/2004 | Grunewald |

OTHER PUBLICATIONS

L.R. Herlinger et al., "TEM Sample Preparation Using a Focused Ion Beam and a Probe Manipulator," Proceedings of the International Symposium for Testing and Failure Analysis, Nov. 18-22, 1996, pp. 199-205, Los Angeles, CA.

* cited by examiner

*Primary Examiner*—Jack I Berman
*Assistant Examiner*—Andrew Smyth
(74) *Attorney, Agent, or Firm*—The Webb Law Firm

(57) ABSTRACT

Method and equipment permitting one to easily prepare a good thin-film specimen adapted for observation are offered. The equipment has an ion gun tilted left and right repeatedly to etch a specimen material by an electron beam tilted left and right by 1.5° about the z-axis. Then, the ion gun is tilted left and right plural times to ion etch the specimen material. Since a portion of the specimen material is especially heavily etched, a through-hole is formed in the specimen material. A thin film having a thickness of about 100 Å is formed around the through-hole. This thickness is adapted for TEM (transmission electron microscope) observation.

18 Claims, 12 Drawing Sheets

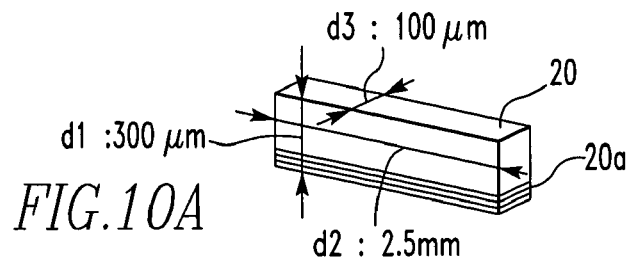
FIG.10A
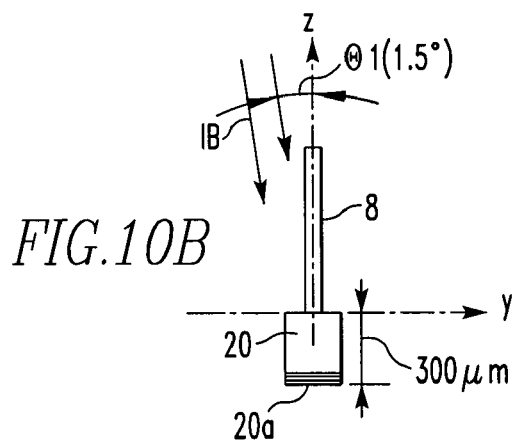
FIG.10B
FIG.10C
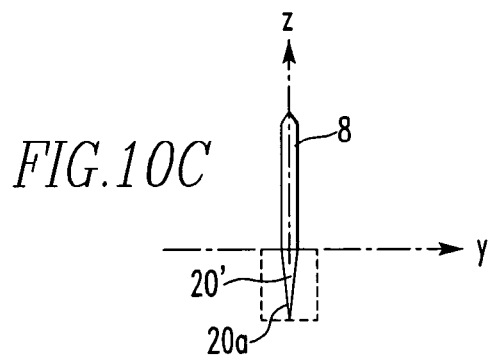
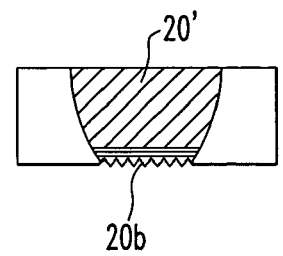
FIG.10D
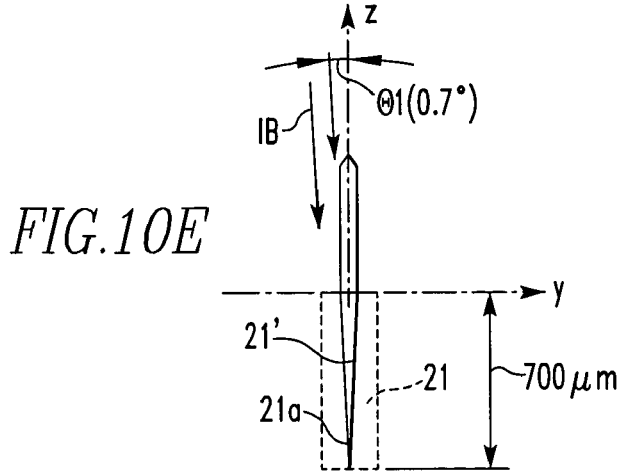
FIG.10E

METHOD AND EQUIPMENT FOR SPECIMEN PREPARATION

BACKGROUND OF THE INVENTION

1. Field of the Invention

The present invention relates to method and equipment for preparing specimens observed with a transmission electron microscope or other instrument.

2. Description of Related Art

The following methods A)-C) have been heretofore known to prepare thin-film specimens observed with a transmission electron microscope (TEM). These methods A)-C) are described below with reference to the drawings.

A) Thinning of a Bulk Specimen (see FIGS. 1A to 1E)

A bulk specimen may be thinned by a procedure consisting of the following steps 1)-5):

1) The specimen is cut to a thickness of about 1 mm and polished. Then, the specimen is roughly polished to a thickness of about 100 μm (FIG. 1A).

2) The specimen is blanked to a diameter of 3 mm (FIG. 1B).

3) One surface of the specimen is mirror polished flat (FIG. 1C).

4) The roughly polished surface of the specimen on the opposite side of the mirror-polished surface is dimpled with a dimple grinder. The center of the formed dimple is formed as a mirror surface having a thickness of about 10 μm (FIG. 1D).

5) The specimen is set in ion milling equipment. Argon ions are directed at the specimen from both sides while rotating the specimen continuously to thin it (FIG. 1E).

B) Preparation of a Section of a Specimen (see FIGS. 2A to 2G)

A section of a specimen, such as a silicon wafer on which an integrated circuit has been formed, is prepared by the procedure consisting of the following steps 1)-7).

1) Plural specimen materials, each 5 to 10 mm square, are cut from a silicon wafer. The specimen materials are bonded together with epoxy resin to form a specimen (FIG. 2A).

2) A cylinder having a diameter of 2.3 mm is blanked out of the specimen by an ultrasonic machine (FIG. 2B).

3) The extracted piece of the specimen having a diameter of 2.3 mm is buried in a metallic pipe having an outside diameter of 3 mm and an inside diameter of 2.3 mm together with epoxy resin (FIG. 2C).

4) The piece of the specimen buried in the metallic pipe is sliced to a thickness of about 1.0 mm by a cutter (FIG. 2D).

5) One surface of the piece of the specimen is mirror polished (FIG. 2E). shielding material to etch the irradiated surface portions around the non-irradiated surface portion while leaving the non-irradiated portion unetched. This method is characterized in that the ion beam is directed at the shielding material and the specimen material from different directions and that the directions of irradiation of the ion beam are so set as to form a thin-film specimen becoming thinner in going downwardly from the non-irradiated surface portion.

Accordingly, in the present invention, a specimen preparation method and a specimen preparation equipment are offered which permit one to easily prepare good thin-film specimens adapted for observation.

Other objects and features of the invention will appear in the course of the description thereof, which follows.

BRIEF DESCRIPTION OF THE DRAWINGS

FIGS. 10A to 10E illustrate the operation of the equipment shown in FIG. 3A;

DESCRIPTION OF THE PREFERRED EMBODIMENTS

Embodiments of the present invention are hereinafter described with reference to the accompanying drawings.

Figure 3A:
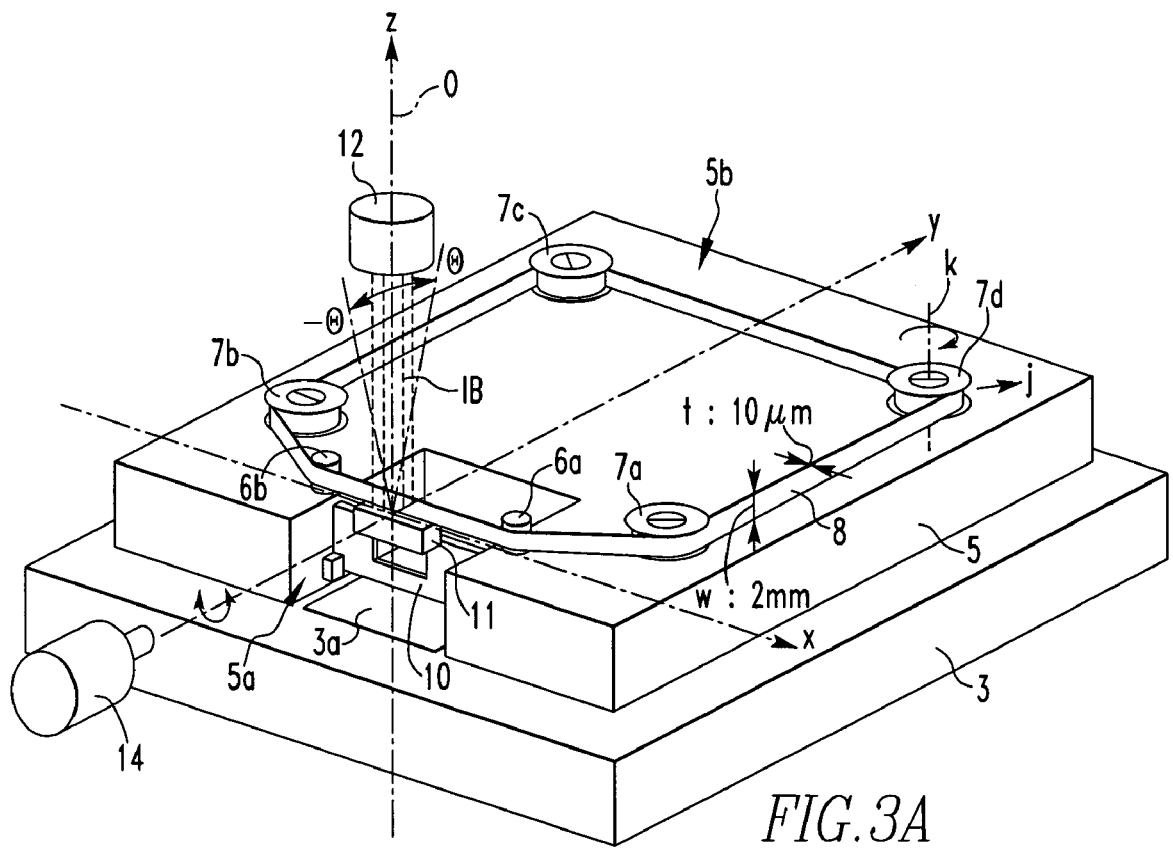
FIGS. 3A and 3B are perspective views of one example of specimen preparation equipment of the present invention.
Figure 3B:
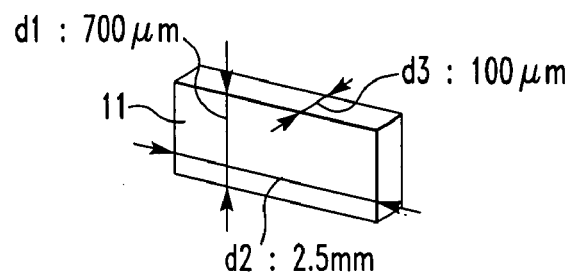
Figure 4A:
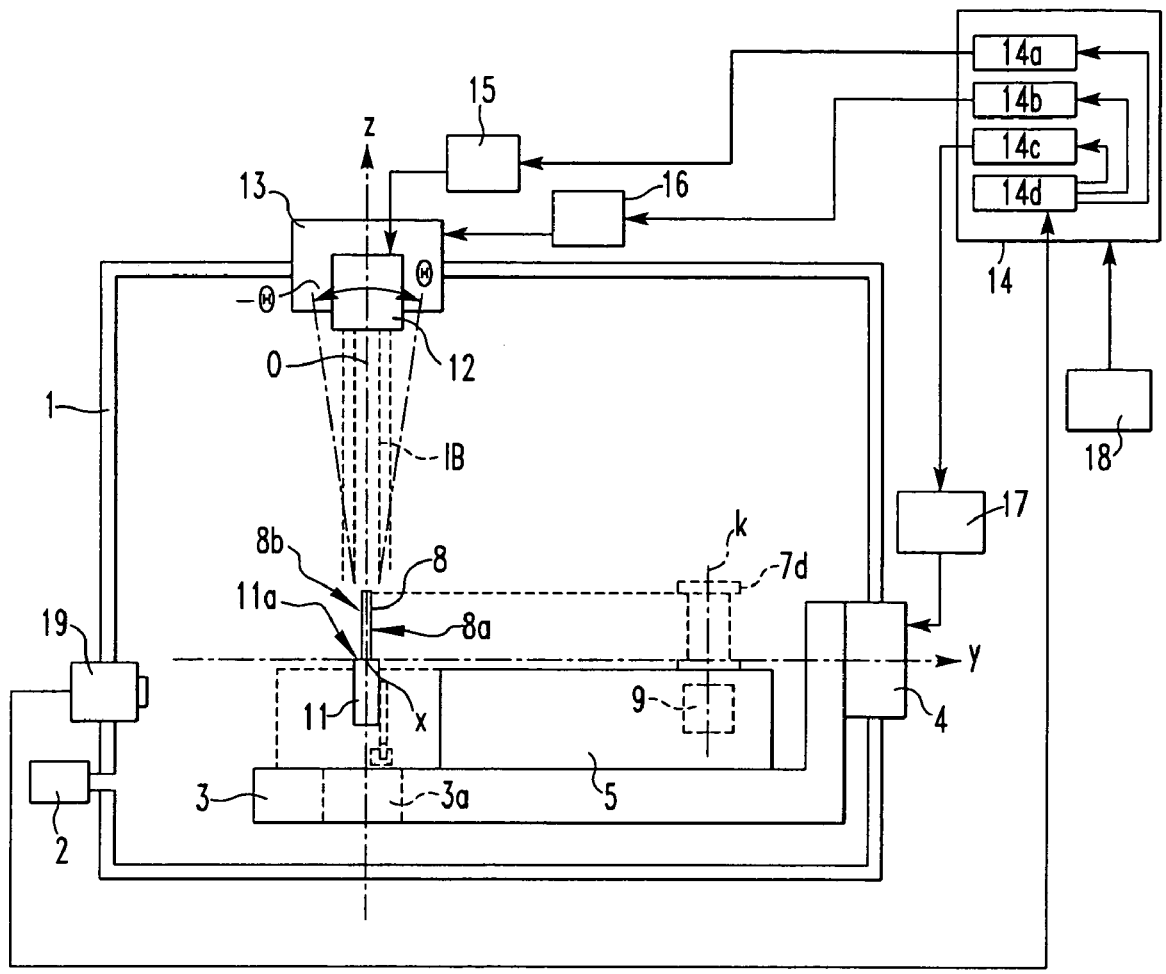
FIGS. 4A to 4B are schematic block diagrams of the whole equipment shown in FIG. 3A.
Figure 4B:
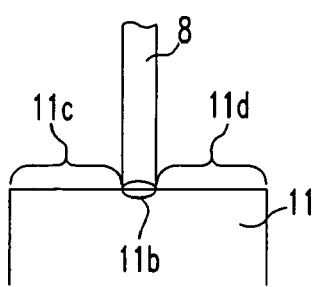

FIGS. 3A and 3B and FIGS. 4A and 4B show one example of specimen preparation equipment of the present invention. FIGS. 3A and 3B show the inside of a vacuum chamber of the equipment. FIGS. 4A and 4B are a cross-sectional view taken along the yz plane of FIG. 3A, showing the whole structure of the specimen preparation equipment of FIG. 3A. The instrumental configuration is first described.

Referring to FIG. 4A, the vacuum chamber is indicated by reference numeral 1. The inside of the chamber 1 is evacuated by a pumping system 2. A specimen stage 3 is mounted to a stage-tilting mechanism 4, which, in turn, is mounted to the vacuum chamber 1. The stage-tilting mechanism 4 is used to tilt the stage 3 left and right about the y-axis. The stage 3 is provided with a beam passage hole 3a to permit passage of an ion beam.

A specimen support 5 is positioned on the specimen stage 3. As shown in FIG. 3A, a cutout 5a is formed in the specimen support 5 to permit passage of the ion beam. Guide pins 6a and 6b are held on the top surface 5b of the specimen support 5 on the opposite sides of the cutout 5a. Four pulleys 7a-7d are disposed over the top surface 5b of the specimen support 5. Of these four pulleys, the pulleys 7a-7c are held to the top surface 5b of the specimen support 5. The remaining pulley 7d is pulled in a direction indicated by the arrow j by a spring (not shown) and mounted to the specimen support 5.

An annular ion beam-shielding material or belt (or ribbon or tape) 8 is trained around the pulleys 7a-7d and guide pins 6a, 6b. The shielding belt 8 is made of an amorphous metal, such as nickel-phosphorus (more than 10% phosphorus). The thickness t of the shielding belt 8 is about 10 μm. The width w is about 2 mm. As described previously, the pulley 7d is pulled by the spring in the direction indicated by the arrow j and so the shielding belt 8 caught to the pulley 7d is stretched without slack over one circle. The pulley 7d is rotated about an axis k by rotation of an electric motor 9 (see FIG. 4A) incorporated in the specimen support 5. When the pulley 7d is rotated in this way, the shielding belt 8 caught to the pulley 7d is automatically fed.

Referring still to FIG. 3A, a specimen holder 10 holds a specimen material 11 and is set in the cutout 5a formed in the specimen support 5. As shown in the lower inset to FIG. 3B, the vertical dimension $d_1$ of the specimen material 11 is about 700 μm. The lateral dimension $d_2$ is about 2.5 mm. The thickness $d_3$ is about 100 μm. The specimen material 11 has been cut out from a bulk specimen and roughly polished. The specimen material 11 is bonded to the specimen holder 10 with adhesive.

Since the specimen material 11 and shielding belt 8 are placed in position over the specimen support 5 in this way, the shielding belt 8 guided by the guide pins 6a and 6b are placed vertically over the specimen material 11 as shown in FIG. 3A and FIG. 4A. As shown in FIG. 4A, the shielding belt 8 stretched over the specimen material 11 crosses the z-axis. The right side surface 8a and left side surface 8b of the shielding belt 8 are parallel to the z-axis. Under the condition shown in FIG. 4A (i.e., the specimen stage is not tilted at all), the longitudinal direction of the portion of the shielding belt 8 stretched over the specimen material 11 is coincident with the x-axis direction.

On the other hand, in the state shown in FIG. 4A, the top surface 11a of the specimen material 11 is perpendicular to the z-axis and located on the y-axis. The gap between the top surface 11a of the specimen material 11 and the shielding belt 8 is only about 10 to 30 μm. Because the shielding belt 8 is located over and close to the specimen material 11 in this way, a non-irradiated portion 11b not irradiated with the ion beam is formed on the surface of the specimen material 11 as shown in FIG. 4B. Also, irradiated portions 11c and 11d irradiated with the ion beam are formed on the surface on the opposite sides of the non-irradiated portion 11b. The non-irradiated portion 11b is a specimen surface portion shielded by the shielding belt 8, and is not irradiated with the ion beam emitted from an ion gun 12 described below.

The ion gun 12 is held to a gun-tilting mechanism 13, which, in turn, is mounted to the top of the vacuum chamber 1 as shown in FIG. 4A. In the state shown in FIG. 4A, the optical axis O of the ion gun 12 is coincident with the z-axis. The tilting mechanism 13 is designed to tilt the ion gun 12 left and right by θ° about the z-axis. That is, the tilting mechanism tilts the ion gun 12 in the −y-direction and y-direction by θ° about the z-axis. A gas ion gun is used as the ion gun 12. For example, this gas ion gun releases Ar ions by ionizing Ar gas by discharging.

Referring also to FIG. 4A, a central controller 14 incorporates a gun control circuit 14a, a gun tilt control circuit 14b, a stage tilt control circuit 14c, and an etch end decision circuit 14d. The central controller 14 is electrically connected with a voltage source 15 for the ion gun 12, a tilt driver 16 for driving the gun-tilting mechanism 13, a tilt driver 17 for driving the stage-tilting mechanism 4, and an input device 18 consisting of a keyboard and a mouse.

Referring still to FIG. 4A, a TV camera 19 is mounted in the vacuum chamber 1. The camera 19 is used to observe the etched section of the specimen material 11 from the −y-direction. The image signal from the TV camera 19 is supplied to the etch end decision circuit 14d of the central controller 14.

The instrumental configuration shown in FIG. 3A and FIG. 4A has been described so far. The operation is described below.

When an operator makes an entry indicating "start of etching" from the input device 18 shown in FIG. 4A, the gun tilt control circuit 14b of the central controller 14 sends a tilt signal $θ_1$ to the tilt driver 16 to tilt the ion gun 12 to the left (−y-direction) by angle $θ_1$ (e.g., 1.5°). In response to the tilt signal $θ_1$, the tilt driver 16 tilts the gun-tilting mechanism 13. As a result, the ion gun 12 tilts to the left by 1.5° about the z-axis. The value of the tilt angle $θ_1$ (1.5°) has been previously entered and set by the operator from the input device 18.

Figure 5:
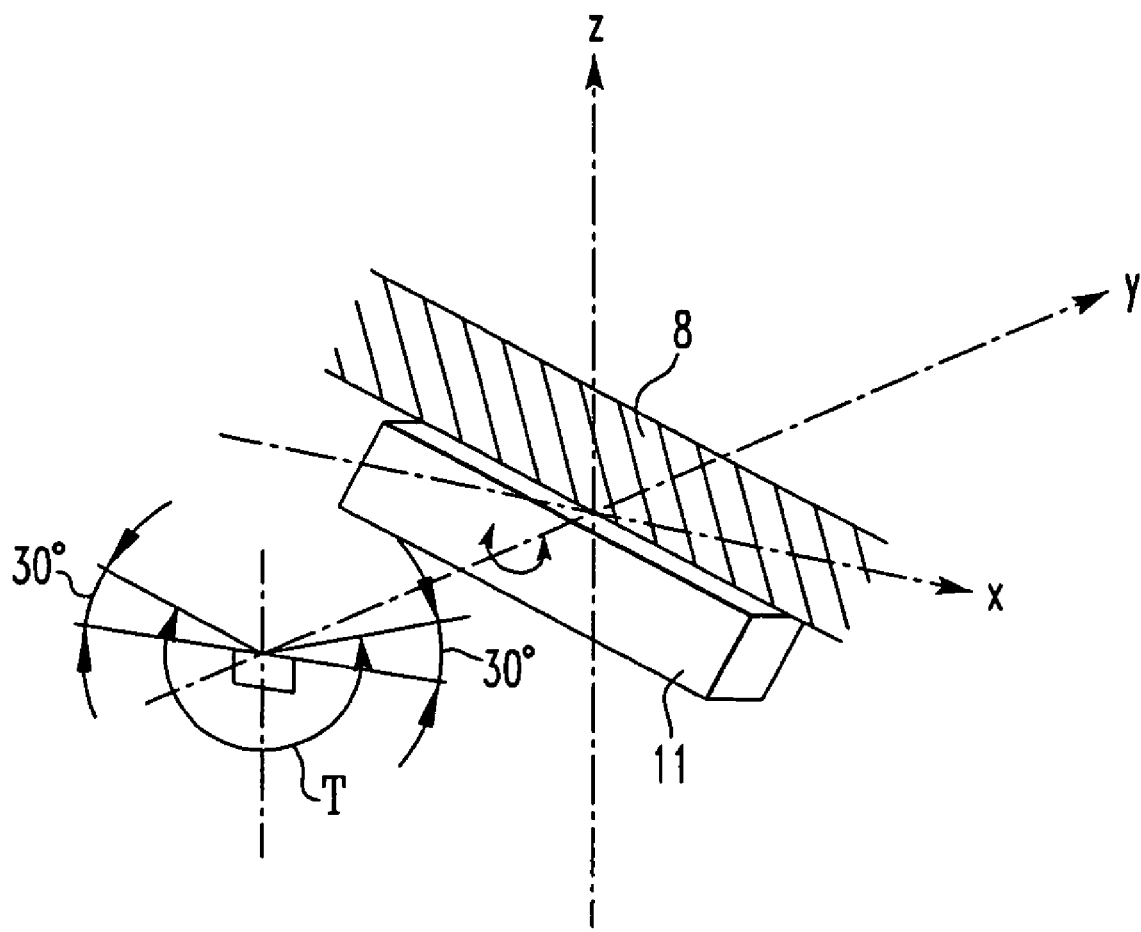
FIG. 5 is a diagram illustrating the operation of the equipment shown in FIG. 3A.

When the aforementioned entry indicating "start of etching" is made, the stage tilt control circuit 14c sends a tilt signal $θ_t$ to the tilt driver 17 to tilt the stage 3 to and fro about the y-axis. For example, the tilt signal $θ_t$ is sent to the tilt driver 17 to repeat tilt of one reciprocation of ±30°. For example, it takes 30 seconds to make one reciprocating tilt. The tilt driver 17 tilts the stage-tilting mechanism 4 according to the tilt signal $θ_t$. As a result, the specimen material 11 is repeatedly and reciprocatively tilted together with the shielding belt 8 as indicated by the arrow T, as shown in FIG. 5. The values of the tilt angle ±30° and tilt time of 30 seconds have been previously entered and set by the operator from the input device 18.

When the aforementioned input indicating "start of etching" is made, the gun control circuit 14a of the central controller 14 sends a signal to the voltage source 15 to emit the ion beam $I_B$ from the ion gun 12. The voltage source 15 applies a given voltage between the electrodes of the ion gun 12 to release the ion beam $I_B$. As a result, as shown in FIG. 6A, the beam $I_B$ is released from the ion gun 12 that is tilted to the left by the angle $θ_1$ (1.5°) about the z-axis.

Figure 6A:
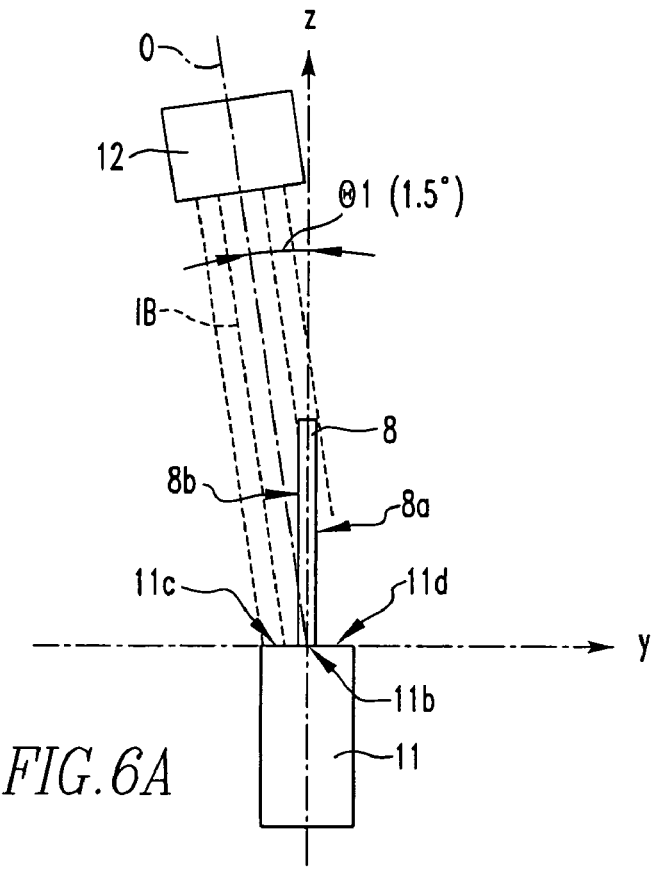
FIGS. 6A and 6B are diagrams illustrating the operation of the equipment shown in FIG. 3A.

The ion beam $I_B$ emitted from the ion gun 12 and tilted to the left by the angle $θ_1$ (1.5°) about the z-axis hits the shielding belt 8 and specimen material 11 obliquely from the left upper side of the shielding belt 8 as shown in FIG. 6A. This beam irradiation is performed for a given time (e.g., 5 minutes). The specimen material 11 is ion etched while tilted about the y-axis. Consequently, if a substance m that is not easily ion etched is present within the specimen material, the portion of the specimen shielded from the ion beam by the material m is also etched. Therefore, it is unlikely that an unetched specimen portion located behind the substance m (on the side facing away from the ion gun) forms a stripe.

Figure 1A:
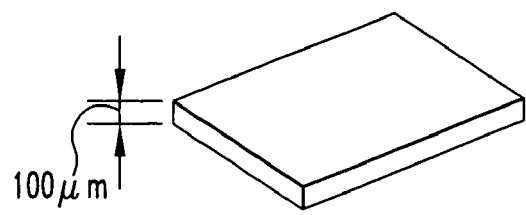
FIGS. 1A to 1E illustrate one conventional method of specimen preparation.
Figure 1B:
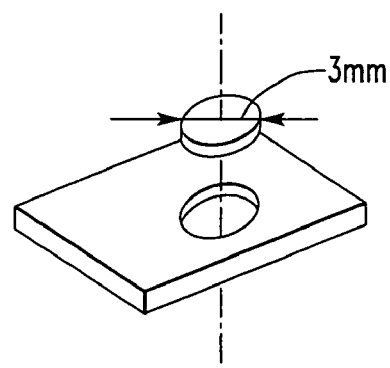
Figure 1C:
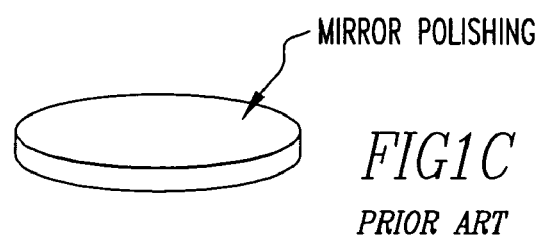
Figure 1D:
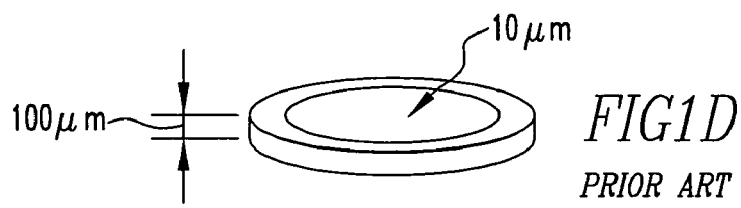
Figure 1E:
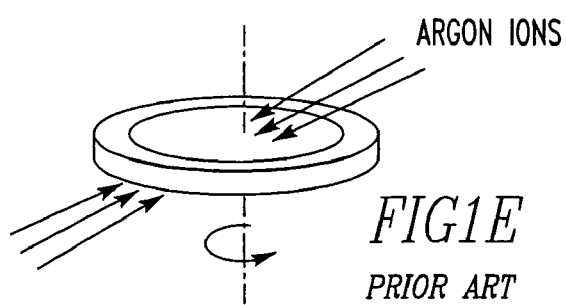
Figure 2A:
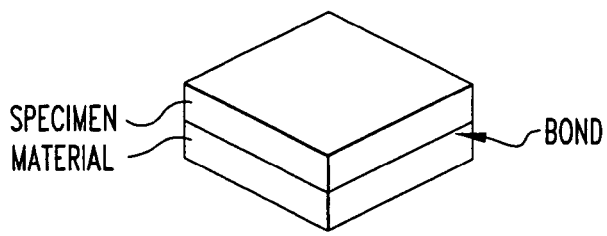
FIGS. 2A to 2G illustrate another conventional method of specimen preparation.
Figure 2B:
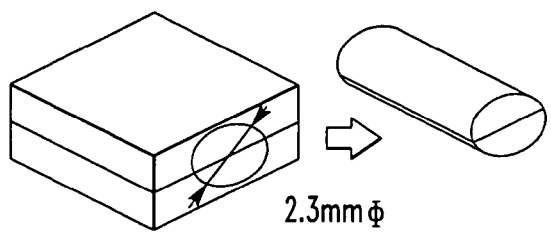
Figure 2C:
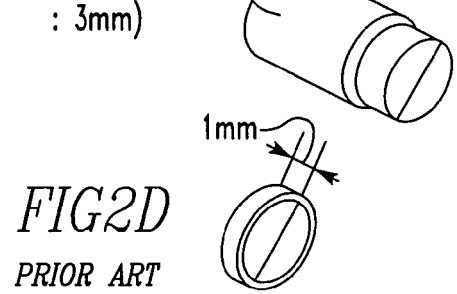
Figure 2D:
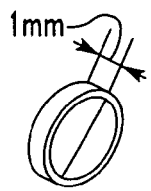
Figure 2E:
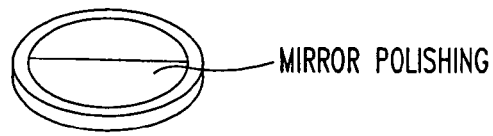
Figure 2F:
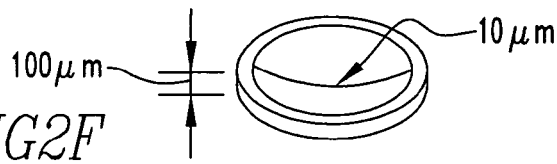
Figure 6B:
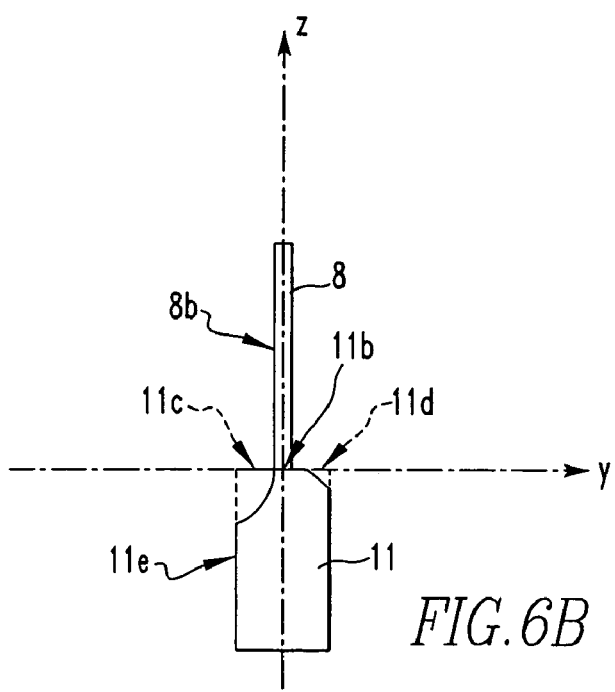

FIG. 6B shows the specimen material 11 after a lapse of 5 minutes from the start of the ion etching. As shown in this figure, the surface portions 11c and 11d irradiated with the beam $I_B$ have been ion etched. On the other hand, the surface portion 11b that is shielded by the shielding belt 8 and not irradiated with the beam $I_B$ is left unetched. Since the beam hits the specimen material 11 from the left upper side of the shielding belt 8, the irradiated surface 6) The surface of the specimen piece on the opposite side of the mirror-polished surface is polished roughly to make the specimen piece have a thickness of about 100 μm. Then, the roughly polished surface of the specimen piece is dimpled with a dimple grinder. The center of the dimple is finished to a mirror surface having a thickness of about 10 μm (FIG. 2F).

Figure 2G:
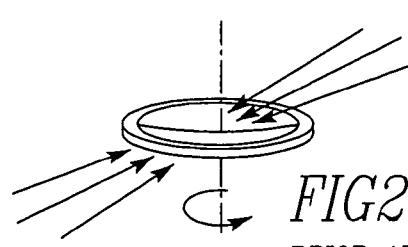

7) The specimen is set in ion milling equipment. Argon ions are directed at the specimen piece from both sides while rotating the specimen piece continuously to thin it (FIG. 2G).

C) Method Described in Japanese Patent No. 3,263,920

In this method, a shielding material is placed over a specimen. A beam of ions is directed at the shielding material and at the specimen from above the shielding material. The portions of the specimen which are not shielded by the shielding material are ion etched. At this time, the shielding material is moved in two steps over the specimen to etch it such that a thin-film specimen can be produced.

Where a specimen is prepared by the method A) or B) described above, considerable skill is necessary. Even a skilled person cannot easily prepare specimens. Furthermore, where a specimen in which soft and hard materials are mixed is mechanically polished with a dimple grinder, the polish speed differs between the hard and soft portions. Consequently, it is difficult to mirror polish the specimen surface flat. In addition, when the specimen is mechanically polished with a dimple grinder, considerable load is applied to the specimen, distorting the specimen crystal.

With the method C) using a shielding material, it is difficult to accurately move the shielding material such that a thin-film specimen is produced. It is not assured that a desired thin-film specimen will be obtained.

SUMMARY OF THE INVENTION

It is an object of the present invention to provide specimen preparation method and specimen preparation equipment permitting one to easily prepare a good thin-film specimen adapted for observation.

A specimen preparation method which achieves the above-described object in accordance with the present invention starts with placing a shielding material over a specimen material to form a non-irradiated portion and irradiated portions on a surface of the specimen material. The irradiated portions are located around the non-irradiated portion. An ion beam is directed at the shielding material and at the specimen material from above the portion 11c is more etched than the irradiated surface portion 11d. Furthermore, the irradiated surface portion 11c is etched more deeply inwardly (on the z-axis side) than the irradiated surface portion 11d.

Although the shielding belt 8 is made of a material that is not easily ion etched, the top portion of the shielding belt 8 is slightly ion etched as shown in FIG. 6B. On the other hand, the left side surface 8b of the shielding belt 8 and the left side surface 11e of the specimen material 11 are little etched, because the beam $I_B$ hits these surfaces 8b and 11e at a quite small incident angle of 1.5°.

After the specimen material 11 is irradiated with the ion beam from the left upper side of the shielding belt 8 in this way, the gun tilt control circuit 14b sends the tilt signal 01 to the tilt driver 16 to tilt the ion gun 12 to the right (in the y-direction) by the angle $\theta_1$ of 1.5°. In response to the tilt signal $\theta_1$, the tilt driver 16 tilts the gun-tilting mechanism 13. As a result, the gun 12 tilts to the right by 1.5° about the z-axis.

Figure 7A:
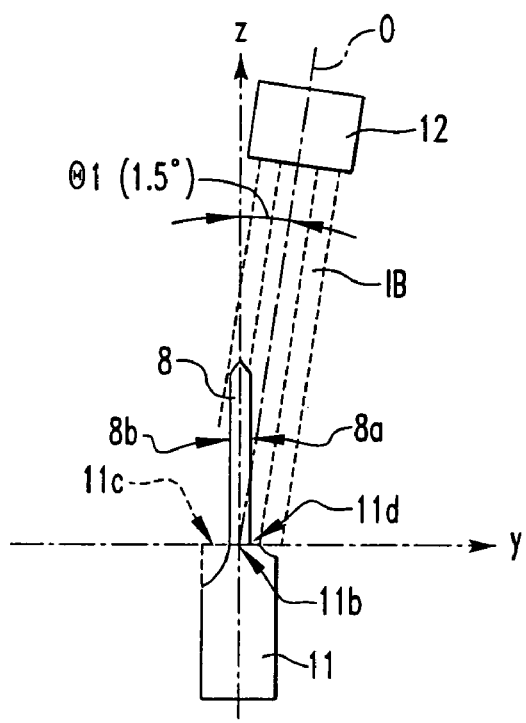
FIGS. 7A and 7B are diagrams illustrating the operation of the equipment shown in FIG. 3A.

As a result of the tilt of the ion gun 12, the ion beam $I_B$ tilted to the right by the angle $\theta_1$ of 1.5° about the z-axis impinges on the shielding belt 8 and the specimen material 11 obliquely from the right upper side of the shielding belt 8 as shown in FIG. 7A. This irradiation is performed for a given time (e.g., 5 minutes). The specimen material 11 is ion etched while tilted together with the shielding belt 8 in the same way as in the above-described process.

Figure 7B:
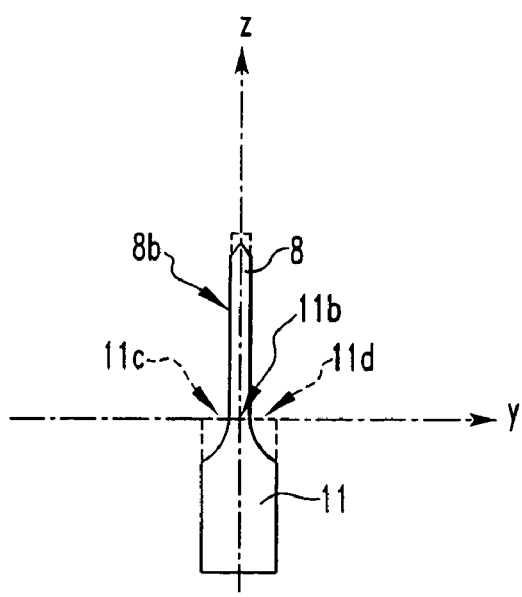

FIG. 7B shows the specimen material 11 after the ion gun 12 has been tilted to the right and the specimen material 11 was irradiated with the ion beam for 5 minutes. As shown in FIG. 7B, the irradiated surface portion 11d of the material 11 has been etched greatly. On the other hand, the non-irradiated surface portion 11b which has been shielded by the shielding belt 8 and was prevented from being irradiated with the beam $I_B$ is left unetched.

Figure 8A:
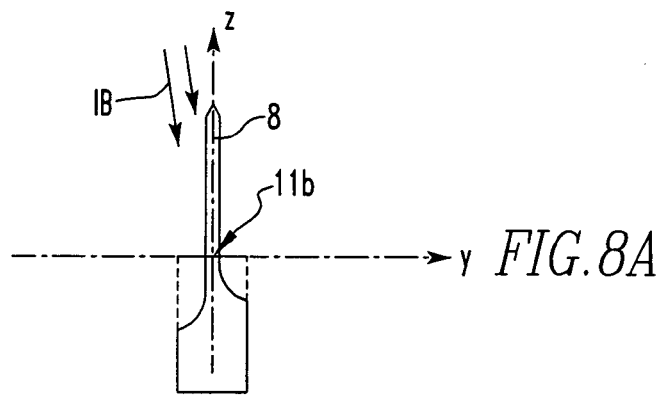
FIGS. 8A to 8E are diagrams illustrating the operation of the equipment shown in FIG. 3A.
Figure 8B:
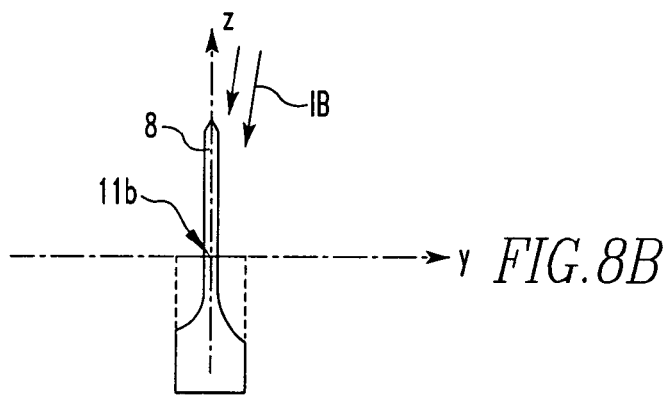
Figure 8C:
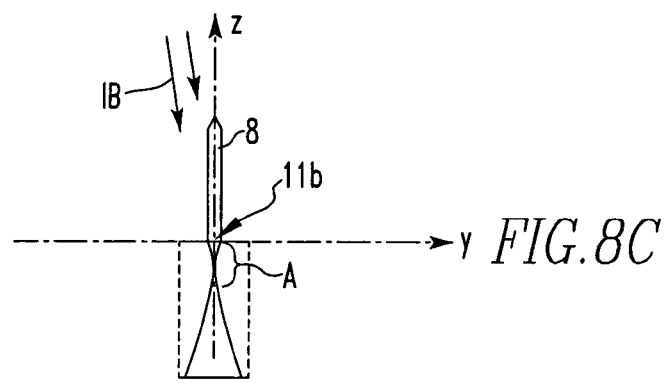

Subsequently, the ion gun 12 is similarly tilted left and right repeatedly. The specimen material 11 is etched by the ion beam $I_B$ tilted by 1.5° left and right about the z-axis. The specimen material 11 being etched is shown in FIGS. 8A to 8C. After the state shown in FIG. 7B, the specimen material 11 is etched as shown in FIG. 8A. Then, the specimen material 11 is etched as shown in FIG. 8B. Thereafter, the ion gun 12 is tilted left and right plural times and the specimen material 11 is etched. The specimen material 11 is etched as shown in FIG. 8C. As shown in FIGS. 8A-8C, the non-irradiated surface portion 11b of the specimen material 11 is left unetched. Meanwhile, the portions of the specimen material which are located around the non-irradiated surface portion 11b are gradually etched. Portion A of the specimen material 11 is reduced in thickness in going downwardly (–z-direction) of the non-irradiated surface portion 11b as shown in FIG. 8C.

Figure 8D:
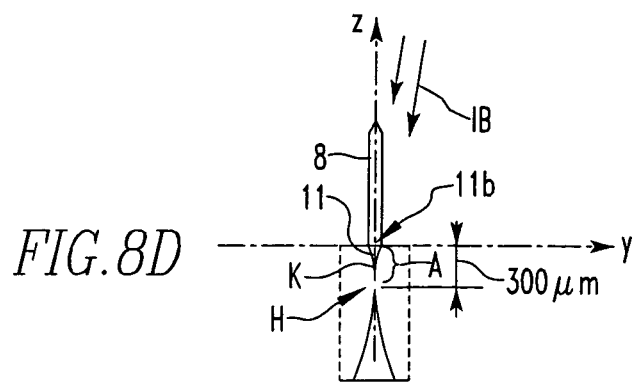
Figure 8E:
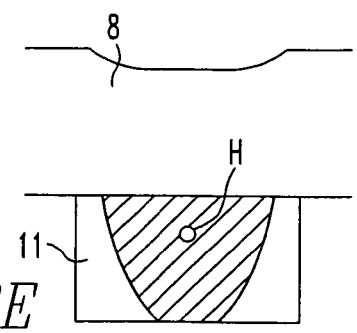

FIG. 8D shows the state in which the sense of the ion gun 12 is varied after the state shown in FIG. 8C and then the specimen material 11 is still being irradiated with the ion beam $I_B$. Since the portion A of the specimen material 11 shown in FIG. 8C is further ion etched, a through-hole H is formed in the specimen material 11 as shown in FIG. 8D. The position of this hole H is at a distance of about 300 μm from the top surface of the specimen material 11. The position where the through-hole H is formed is closely related to the tilt angle of the ion gun 12. That is, the position of the through-hole H is affected greatly by the direction from which the shielding belt 8 and the specimen material 11 are irradiated with the beam $I_B$. In this embodiment, the specimen material 11 is etched by the ion beam $I_B$ tilted left and right by 1.5° about the z-axis and so the through-hole H is formed in the position shown in FIG. 8D. FIG. 8E shows the specimen material 11 of FIG. 8D as viewed from the –y-direction (from the side of the TV camera 19 of FIG. 4A). The camera 19 shown in FIG. 4A images the specimen material 11 from the front side from the starting point of ion etching. The image signal from the TV camera 19 is sent to the etch end decision circuit 14d of the central controller 14. The decision circuit 14d constantly monitors variation of the shape of the specimen material 11. If the decision circuit 14d detects that the through-hole H is formed in the specimen material 11 as shown in FIG. 8D according to the image signal sent in from the TV camera 19, the decision circuit sends an Etch End signal to the gun control circuit 14a. On receiving the Etch End signal, the gun control circuit 14a sends a signal to the voltage source 15 to stop the ion irradiation. Thus, the beam emission from the ion gun 12 is stopped.

The Etch End signal is also sent to the gun tilt control circuit 14b and to the stage tilt control circuit 14c from the etch end decision circuit 14d. These control circuits 14b and 14c send tilt stop signals to the tilt drivers 16 and 17, respectively. Consequently, the tilt of the ion gun 12 and the tilt of the stage 3 are stopped.

The thin-film specimen 11 of the present invention as shown in FIGS. 8D and 8E is finished as described so far. As shown in FIG. 8D, the portion A of the finished specimen becomes thinner in going downwardly from the non-irradiated surface portion 11b. The portion K located around the through-hole H is a thin film of about 100 Å. The thickness of the thin-film portion K is adapted for TEM observation.

In the present invention using argon ions, even if soft and hard materials are mixed in the specimen material, the surface of the specimen material can be mirror polished flat. Therefore, the surface of the thin-film portion K in FIG. 8D is mirror finished flat. Since the shielding belt 8 is made of an amorphous metal, if the belt 8 is ion etched, the surface is prevented from becoming uneven. This is also important for flattening and mirror-finishing of the surface of the thin-film portion K.

Furthermore, in the aforementioned specimen preparation according to the present invention, a dimple grinder is not used, unlike the prior art. Instead, argon ions which can result in a quite low level of damage to the specimen are used. Therefore, if the specimen material is irradiated with argon ions and mirror polished, the specimen crystal is prevented from being distorted, unlike where a dimple grinder is used.

In this way, in the thin-film specimen 11 prepared in accordance with the present invention and shown in FIG. 8D, the specimen crystal is not distorted. The surface of this specimen has been mirror polished flat and is adapted for TEM observation. Accordingly, a good TEM image of the thin-film portion K can be obtained by transporting the thin-film specimen 11 finished in this way into a TEM and irradiating the thin-film portion K with an electron beam.

In addition, no skill is necessary in preparing a specimen in accordance with the present invention as described above. Anyone can prepare a good thin-film specimen easily.

Figure 9:
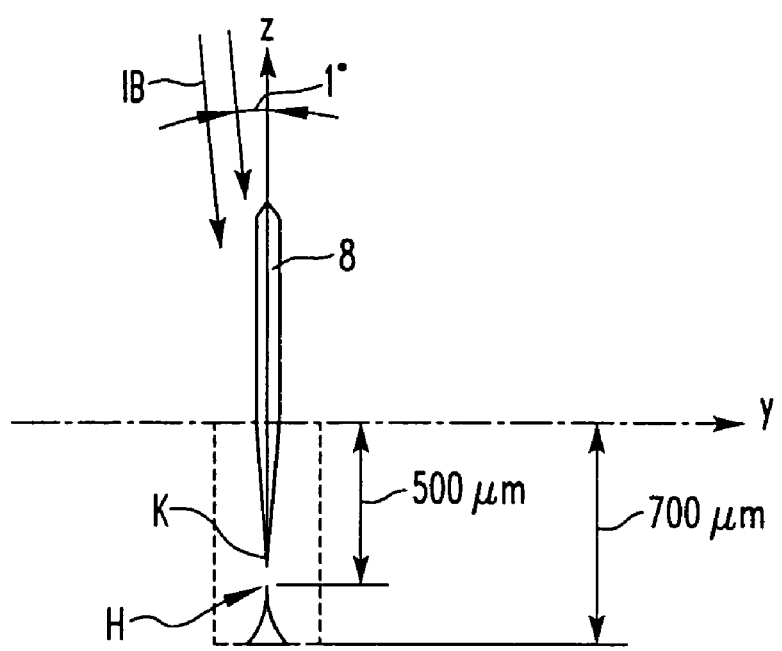
FIG. 9 is a diagram illustrating the operation of the equipment shown in FIG. 3A.

In the above-described embodiment, the specimen material is etched by the ion beam tilted left and right by 1.5° about the z-axis. A thin-film specimen as shown in FIG. 9 is produced by etching the specimen material by the ion beam that is tilted left and right, for example, by 1° about the z-axis. In this case, the through-hole H is formed at a position located at a distance of about 500 μm from the top surface of the specimen material. Since the tilt angle of the ion beam is reduced, the area of the thin-film portion K adapted for TEM observation is widened accordingly compared with the case of FIG. 8D. Therefore, if the thin-film specimen shown in FIG. 9 is transported into the TEM and observed, the specimen can be observed at a lower magnification than the specimen shown in FIG. 8D.

Furthermore, in the above embodiment, the specimen material is etched by the ion beam tilted left and right about the z-axis. The step of etching the specimen material by the ion beam traveling on the z-axis (i.e., the ion beam is directed from immediately above the shielding belt) and the step of etching the specimen material by the ion beam tilted either left or right about the z-axis by 3°, for example, may be alternately and repeatedly carried out.

A case where a specimen material cut out from a bulk specimen is thinned using the equipment shown in FIGS. 3A and 4A has been described so far. A case where a specimen material cut out from a silicon wafer or the like is thinned using the equipment of FIGS. 3A and 4A and a section of the specimen is prepared is described below.

In this case, a specimen material 20 of 300 μm ($d_1$)×2.5 mm ($d_2$)×100 μm ($d_3$) is first prepared as shown in FIG. 10A. This specimen material 20 has been cut out from a silicon wafer and roughly polished. The material 20 has a multilayered lower portion 20a. The purpose is to thin the multilayered portion 20a for preparing a section of the specimen. The specimen material 20 cut out in this way is set in the specimen holder 10. The holder is attached to the specimen support 5.

FIG. 10B shows the specimen material 20 and shielding belt 8 which have been set on the specimen support 5 (not shown in this figure). As shown in FIG. 10B, the multilayered portion 20a of the specimen material 20 is located at a distance of about 300 μm from the shielding belt 8. The ion gun 12 is repeatedly tilted left and right in the same way as in the above-described process. The specimen material 20 is etched by the ion beam $I_B$ tilted left or right by 1.5° about the z-axis. The specimen material 20 is tilted about the y-axis in the same way as in the process described above.

FIG. 10C shows a finished thin-film specimen 20'. FIG. 10D is a view of the thin-film specimen of FIG. 10C as viewed from the −y-direction. As shown in FIG. 10C, the thin-film specimen 20' becomes thinner in going away from the shielding belt 8. The multilayered portion 20a is thinnest. The thickness is about 100 Å, which is adapted for TEM observation.

At this time, the end of the ion etching is determined by detecting the shape of the edge of the lower end of the specimen material. That is, when the etch end decision circuit 14d detects that the edge 20b has been zigzagged by ion etching as shown in FIG. 10D, emission of the ion beam from the ion gun is stopped.

In this embodiment, a specimen material having a vertical dimension $d_1$ of 300 μm is prepared. The material is etched by the ion beam tilted to the left or right by 1.5° about the z-axis. Alternatively, if a specimen material 21 having a vertical dimension $d_1$ of 700 μm is prepared as shown in FIG. 10E, and if the specimen material 21 is etched by an ion beam tilted to the right or left by 0.7° about the z-axis, a specimen section 21' in which the multilayered portion 21a is thinnest can be prepared.

The operation of the equipment shown in FIGS. 3A and 4A has been described so far. It is to be understood that the invention is not limited to the above embodiment and that other modified embodiments are embraced within the invention.

For instance, in the above embodiment, the direction of tilt of the ion gun 12 is switched between left and right at intervals of five minutes. The interval may be shortened in approaching the end of the ion etching. For example, the direction of tilt of the ion gun 12 may be switched between left and right at intervals of 30 seconds during a final period of the etching. In this case, if the previously-etched surface of the specimen surface on the opposite side of the presently-etched surface is contaminated due to splashing matter produced by the present etching, the level of contamination would not be high enough to hinder TEM observation.

Additionally, in the above embodiment, the ion gun 12 is tilted about the x-axis. The gun 12 may also be tilted about an axis q that is located close and parallel to the x-axis.

Further, in the above embodiment, the stage 3 is tilted about the y-axis. Alternatively, the stage 3 may also be tilted about an axis r that is located close and parallel to the y-axis. For example, the specimen material may be irradiated with an ion beam while tilting the material either about the axis r that is substantially perpendicular to the surface of a thin film to be prepared or about an axis parallel to the axis r.

Yet additionally, in the above embodiment, the thickness of the shielding belt 8 is 10 μm. The used shielding belt 8 may have a thickness of 5 to 30 μm, for example. Still additionally, in the above embodiment, the width of the shielding belt 8 is 2 mm. The used shielding belt 8 may have a width of 1.5 to 2.5 mm, for example.

Yet further, in the above embodiment, the ion gun 12 is tilted by 1.5°, 1°, or 0.7° about the z-axis. The invention is not limited to these tilt angles. The tilt angle, i.e., direction in which the ion beam is directed, may be appropriately set according to the thickness of the shielding belt and the dimension of the specimen material such that the prepared thin-film specimen becomes thinner in going downwardly from the non-irradiated surface portion. For example, an ion beam impinging on a specimen material obliquely from the right upper side of the shielding material may be appropriately tilted by 1° to 10° with respect to an ion beam hitting the specimen material obliquely from the left upper side of the shielding belt.

Still further, in the above embodiment, the ion gun 12 is tilted left and right. Two ion guns may be mounted. An ion beam produced from one ion gun may be directed at the shielding belt and at the specimen material obliquely from the left upper side of the shielding belt. An ion beam produced from the other gun may be directed at the shielding material and at the specimen material obliquely from the right upper side of the shielding belt. In this scheme, a specimen can be prepared approximately at a double speed compared with the speed in the above embodiments.

Figure 11:
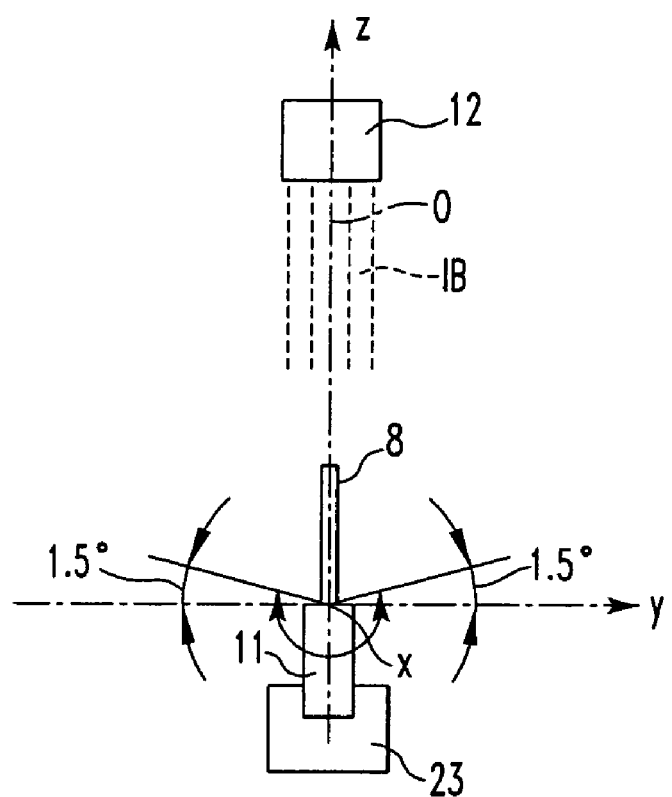
FIG. 11 is a diagram illustrating another embodiment of the present invention.

Still, moreover, in the above embodiment, the ion gun 12 is tilted left and right about the z-axis. The ion gun may be fixed without tilting it. The specimen material and the shielding belt may be tilted together. For example, as shown in FIG. 11, the ion gun may be so fixed that its optical axis O is coincident with the z-axis. An ion beam $I_B$ may be made to hit the specimen material 11 while tilting a tilting means 23 left and right about the x-axis, the tilting means carrying the specimen material 11 and shielding belt 8 thereon.

In this case, the specimen material 11 is irradiated with the ion beam for 5 minutes under conditions where the material 11 is tilted to the left by 1.5°, for example. Then, the material 11 is tilted to the right by 1.5°, for example. Under this condition, the material 11 is irradiated with the beam for 5 minutes. These steps of ion irradiation are repeatedly carried out. During the ion irradiation, the specimen material 11 and shielding belt 8 are tilted about the y-axis as mentioned previously. Instead of tilting together the specimen material 11 and shielding belt 8 left and right about the x-axis, only the specimen material 11 may be tilted left and right about the x-axis.

In the equipment shown in FIGS. 3A and 4A, safety measures are taken to prevent the shielding belt 8 from breaking if ion etching is done for a long time. That is, in the equipment shown in FIGS. 3A and 4A, a power off period in which the ion power supply is turned off is set according to the used accelerating voltage of the ion gun. In a case where etching end is not judged by the etch end decision circuit 14d even if the power off period has passed since the start of the etching, the power supply of the ion gun is forcedly turned off. The power off period is set shorter in increasing the accelerating voltage.

Figure 12A:
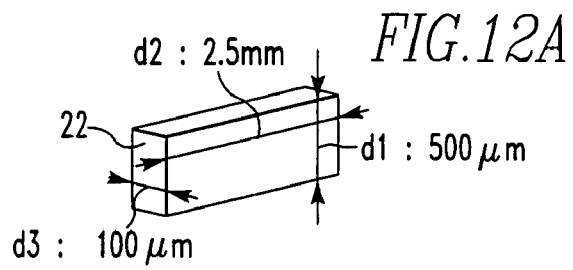
FIGS. 12A to 12D illustrate a further embodiment of the present invention.

The equipment shown in FIGS. 3A and 4A can be used as pretreatment equipment for preparation of a specimen, the pretreatment equipment depending on a focused ion beam (FIB) system. This FIB system processes a specimen by scanning a focused ion beam, such as a beam of gallium ions, over the specimen in two dimensions. In this case, as shown in FIG. 12A, a parent material 22 of 500 µm ($d_1$)×2.5 mm ($d_2$)×100 µm ($d_3$), for example, is prepared. This parent material 22 is set in the specimen holder 10. The holder 10 is mounted to the specimen support 5.

Figure 12B:
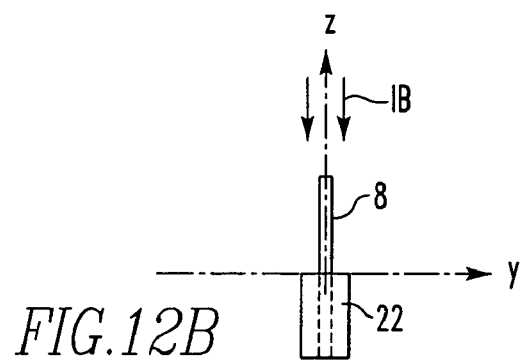
Figure 12C:
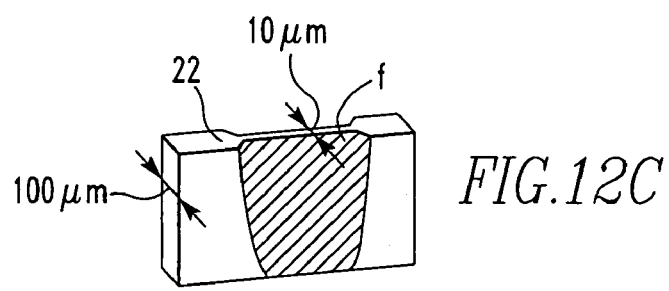

FIG. 12B shows the parent material 22 and the shielding belt 8 which have been set on the specimen support 5 (not shown in this figure). An ion beam $I_B$ is directed at the shielding belt 8 and at the parent material 22 from immediately above the shielding belt 8. That is, ion-beam irradiation is performed under conditions where the tilt angle of the ion gun is 0°. FIG. 12C shows the parent material 22 immediately after the ion-beam irradiation. The thickness of the top portion f is about 10 µm, which is equal to the thickness of the shielding belt 8.

Figure 12D:
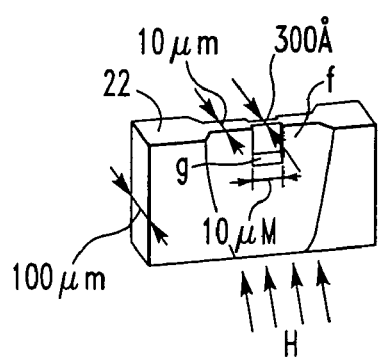

The parent material (specimen material) 22 shown in FIG. 12C is set in the FIB system and the portion f is processed by the FIB technology as shown in FIG. 12D. As a result, a thin film having a thickness of about 300 Å is formed on the specimen material 22. During this FIB processing, the corners of the frontage are obliquely polished to a depth of micrometers (portion g). The rear surface of the specimen material 22 is similarly polished obliquely.

The specimen material 22 processed by FIB processing in this way is set in argon ion beam irradiation equipment different from the equipment shown in FIGS. 3A and 4A. A beam of argon ions is directed at the specimen material 22 from a direction indicated by the arrow H of FIG. 12D. The rear surface is similarly irradiated with a beam of argon ions. The portion thinned to about 300 Å is further etched into a thin film of about 100 Å. The argon ion irradiation removes FIB damage to the specimen. In this way, in this embodiment, the parent material is previously processed to a thickness of about 10 µm using the equipment shown in FIGS. 3A and 4A and so the FIB processing time can be shortened.

Figure 13:
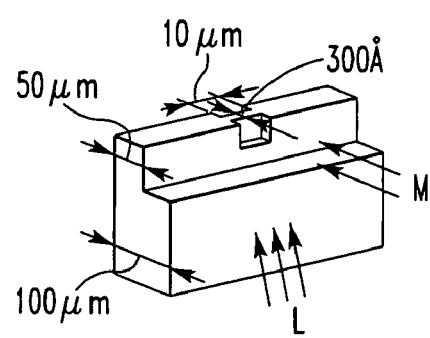
FIG. 13 illustrates a prior art specimen.

In the past, as shown in FIG. 13, a parent material processed to a thickness of about 50 µm by mechanical polishing has been processed by the FIB technology. With mechanical polishing, the thickness can be reduced down to about 50 µm at best. A considerable time has been required to process such a thick parent material having a thickness of 50 µm down to about 300 Å by FIB processing. In contrast, in the present invention, FIB processing can be performed in a short time.

Furthermore, in the prior art specimen material shown in FIG. 13, the portion located around the thin-film portion having a thickness of 300 Å has a considerably large thickness of 50 µm. In addition, with the current FIB processing technology, if the focused ion beam is deflected to the greatest extent, the frontage of the thin-film portion can be increased up to about 10 µm. Accordingly, the prior specimen material shown in FIG. 13 has a narrow frontage and a large depth. If a beam of argon ions is directed at such a specimen material from a direction indicated by the arrow L, the thin-film portion cannot be well thinned in the prior art. Also, damage to the thin-film portion of the specimen due to FIB processing cannot be removed well. If a beam of argon ions were directed at the thin-film portion from the front side as indicated by the arrow M, the thin-film portion would be etched off at high speed, overetching the thin-film portion. For this reason, it has been impossible to perform argon ion beam irradiation from the front side.

On the other hand, in the specimen material of the present invention shown in FIG. 12D, the frontage of the thin-film portion is about 10 µm. The thickness of the portion of the specimen which is located around the frontage is as small as 10 µm. Furthermore, as described previously, the corners of the frontage are obliquely polished to a thickness on the order of micrometers (portion g). Therefore, in the present invention, a thin-film portion is etched by directing a beam of argon ions at the specimen material 22 from a direction indicated by the arrow H in FIG. 12D. Consequently, a thin film having a thickness of about 100 Å is obtained. Because of this argon ion irradiation, damage to the specimen due to FIB processing can be removed completely.

While a case where the equipment shown in FIGS. 3A and 4A is used as pretreatment equipment which employs an FIB system and which is used for specimen preparation has been described so far, the FIB equipment may be incorporated in the equipment shown in FIGS. 3A and 4A to constitute one specimen preparation apparatus. Additionally, this specimen preparation apparatus may be equipped with an argon ion beam irradiation mechanism for removing damage to the specimen due to FIB processing.

Having thus described my invention with the detail and particularity required by the Patent Laws, what is desired protected by Letters Patent is set forth in the following claims.

The invention claimed is:

1. A method of preparing a specimen, comprising the steps of:

placing a shielding material over a specimen material to form a non-irradiated surface portion and irradiated surface portions on the specimen material, the irradiated surface portions being located around the non-irradiated surface portion said shielding material being shaped like a belt, ribbon, or tape, said shielding material being placed over the specimen material; and directing an ion beam relative to said non-irradiated surface portion at the shielding material and at the specimen material from different directions to etch said irradiated surface portions while leaving said non-irradiated surface portion unetched, said ion beam being directed at the shielding material and at the specimen material obliquely relative to said non-irradiated surface portion from the left side of the shielding material or from directly at the shielding material, said ion beam being also directed at the shielding material and at the specimen material obliquely relative to said non-irradiated surface portion from the right side of the shielding material, wherein the directions in which the ion beam is directed are set in such a way as to form a thin-film specimen having a thickness which decreases in going away from said non-irradiated surface portion.

2. A method of preparing a specimen as set forth in claim 1, wherein said shielding material shaped like a belt, ribbon, or tape has a thickness of about 5 to 30μm, and wherein the ion beam is directed at the specimen material obliquely from the right and left sides of the shielding material is tilted at an angle of 1° to 10° with respect to an axis substantially perpendicular to the non-irradiated surface portion of the specimen material.

3. A method of preparing a specimen as set forth in claim 1, wherein the directions in which said ion beam is directed are so set that the specimen becomes thinner in going away from said non-irradiated surface portion and that a hole extending through the specimen is finally formed.

4. A method of preparing a specimen as set forth in claim 1, wherein the ion beam is directed at the specimen material while tilting the specimen material about an axis substantially perpendicular to a surface of the thin film to be formed or about an axis parallel to the first-mentioned axis.

5. A method of preparing a specimen as set forth in claim 4, wherein said specimen material and said shielding material are tilted together.

6. A method of preparing a thin film specimen by processing a parent specimen material by an ion beam, said method comprising the steps of:

placing a shielding material shaped like a belt, ribbon, or tape substantially vertically over the parent material to form a non-irradiated surface portion on the parent material; and directing an ion beam at the shielding material and at the parent material from above the shielding material to etch portions of the parent material that are located on opposite sides of said non-irradiated surface portion.

7. Specimen preparation equipment for preparing a thin-film specimen by processing a specimen material by an ion beam, said specimen preparation equipment comprising:

a shielding material shaped like a belt, ribbon, or tape and placed substantially over the specimen material to form a non-irradiated surface portion and irradiated surface portions on the specimen material, the irradiated surface portions being located on opposite sides of the non-irradiated surface portion;

means for directing an ion beam at a left side surface of the shielding material and at the specimen material obliquely relative to the non-irradiated surface portion from the left side of the shielding material; and means for directing an ion beam at a right side surface of the shielding material and at the specimen material obliquely relative to the non-irradiated surface portion from the right side of the shielding material, wherein directions in which said ion beams are directed are so set as to form a thin-film specimen which becomes thinner in going away from said non-irradiated surface portion.

8. Specimen preparation equipment as set forth in claim 7, wherein said shielding material shaped like a belt, ribbon, or tape has a thickness of about 5 to 30 μm, and wherein the ion beam directed at the specimen material obliquely from the right and left sides of the shielding material tilted at an angle of about 1° to 10° with respect to an axis substantially perpendicular to the non-irradiated surface portion of the specimen material.

9. Specimen preparation equipment as set forth in claim 7, further including means which detects whether there is a hole extending through a portion of the specimen material located under said non-irradiated surface portion and which, if such a hole is detected, stops the ion beam from being directed at the specimen material.

10. Specimen preparation equipment as set forth in claim 8, further including means which detects whether there is a hole extending though a portion of the specimen material located under said non-irradiated surface portion and which, if such a hole is detected, stops the ion beam from being directed at the specimen material.

11. Specimen preparation equipment as set forth in claim 7, further including means for detecting a shape of a lower end of the specimen material and stopping the ion beam from being directed at the specimen material.

12. Specimen preparation equipment as set forth in claim 8, further including means for detecting a shape of a lower end of the specimen material and stopping the ion beam from being directed at the specimen material.

13. Specimen preparation equipment as set forth in claim 7, wherein the ion beam is directed at the specimen material while tilting the specimen material about an axis substantially perpendicular to a surface of a thin film to be formed or about an axis parallel to the first-mentioned axis.

14. Specimen preparation equipment as set forth in claim 8, wherein the ion beam is directed at the specimen material while tilting the specimen material about an axis substantially perpendicular to a surface of a thin film to be formed or about an axis parallel to the first-mentioned axis.

15. Specimen preparation equipment as set forth in claim 13, wherein the specimen material and the shielding material are tilted together.

16. Specimen preparation equipment as set forth in claim 14, wherein the specimen material and the shielding material are tilted together.

17. Specimen preparation equipment as set forth in claim 7, wherein an ion gun emitting the ion beam is tilted, and wherein the ion beam is directed at the shielding material and at the specimen material obliquely from the left upper side of the shielding material and obliquely from the right upper side of the shielding material.

18. Specimen preparation equipment as set forth in claim 7, wherein there are provided first and second ion guns each producing an ion beam, and wherein the ion beam produced from the first ion gun is directed at the shielding material and at the specimen material obliquely from the left upper side of the shielding material and the ion beam produced from the second ion gun is directed at the shielding material and at the specimen material obliquely from the right upper side of the shielding material.

* * * * *

UNITED STATES PATENT AND TRADEMARK OFFICE
CERTIFICATE OF CORRECTION

PATENT NO. : 7,453,073 B2  Page 1 of 1
APPLICATION NO. : 11/237272
DATED : November 18, 2008
INVENTOR(S) : Yoshioka It is certified that error appears in the above-identified patent and that said Letters Patent is hereby corrected as shown below:

Column 11, Line 25, Claim 2, "material is tilted" should read
-- material tilted --

Signed and Sealed this

Twenty-fourth Day of March, 2009

JOHN DOLL
*Acting Director of the United States Patent and Trademark Office*